United States Patent
Murata

(10) Patent No.: US 7,688,056 B2
(45) Date of Patent: Mar. 30, 2010

(54) PARTICLE HAVING MESOPORE LOADED WITH BIOLOGICAL SUBSTANCE, SENSOR INCLUDING THE SAME, AND METHOD FOR DETECTING SPECIMEN

(75) Inventor: Yusuke Murata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 509 days.

(21) Appl. No.: 11/643,838

(22) Filed: Dec. 22, 2006

(65) Prior Publication Data

US 2007/0148044 A1    Jun. 28, 2007

(30) Foreign Application Priority Data

Dec. 27, 2005    (JP)    ............... 2005-375172

(51) Int. Cl.
 *G01R 19/00* (2006.01)
(52) U.S. Cl. ................................. 324/76.11
(58) Field of Classification Search .......... None
 See application file for complete search history.

(56) References Cited

U.S. PATENT DOCUMENTS

| 6,846,546 | B2 | 1/2005 | Kuroda et al. | ............... 428/188 |
| 6,984,414 | B2 | 1/2006 | Miyata | ............... 427/243 |
| 2002/0015985 | A1 | 2/2002 | Takahashi et al. | ............ 435/180 |
| 2005/0048264 | A1 | 3/2005 | Miyata et al. | ............... 428/166 |
| 2006/0062909 | A1 | 3/2006 | Miyata | ............... 427/226 |

FOREIGN PATENT DOCUMENTS

| JP | 2000-139459 | 5/2000 |
| JP | 2002-95471 | 4/2002 |

OTHER PUBLICATIONS

Cabrera et al. "A new monolithic-type HPLC column for fast separations", J. High Resol. Chromatogr. 2000, 23(1):93-99.*
Liu et al. "An amperometric biosensor based on the coimmobilization of horseradish peroxidase and methylene blue on a beta-type zeolite modified electrode", Fresenius J Anal Chem, 2000, 367:539-544.*
Takahashi et al. "Immobilized enzymes in ordered mesoporous silica materials and improvement of their stability and catalytic activity in an organic solvent", Microporous and Mesoporous Materials, 2001, 44-45:755-762.*
Yunpeng Ye, et al., "Polyvalent Carbocyanine Molecular Beacons for Molecular Recognitions", Journal of the American Chemical Society, vol. 126, No. 25, 2004, pp. 7740-7741 (with attached pp. 1-12).
Dongyuan Zhao, et al., "Triblock Copolymer Syntheses of Mesoporous Silica with Periodic 50 to 300 Angstrom Pores", Science, vol. 279, Jan. 23, 1998, pp. 548-552.
Sol-Gel Science, Chapter 10: Surface Chemistry and Chemical Modification, 1989, pp. 662-663.

* cited by examiner

*Primary Examiner*—Karen Cochrane Carlson
*Assistant Examiner*—Bin Shen
(74) *Attorney, Agent, or Firm*—Fitzpatrick, Cella, Harper & Scinto

(57) ABSTRACT

The present invention provides a porous particle loaded with a larger amount of biological substance. A rod-shaped particle according to the present invention includes a plurality of mesopores that crosses the major axis of the rod-shaped particle and that is loaded with the biological substance.

16 Claims, 8 Drawing Sheets

1 μm

11

50 nm

12

50 nm

12

US 7,688,056 B2

PARTICLE HAVING MESOPORE LOADED WITH BIOLOGICAL SUBSTANCE, SENSOR INCLUDING THE SAME, AND METHOD FOR DETECTING SPECIMEN

BACKGROUND OF THE INVENTION

1. Field of the Invention

The present invention relates to a technique for immobilizing a biological substance to stabilize the biological substance. More particularly, the present invention relates to a particle having a mesopore loaded with a biological substance. The particle can be used in a biosensor.

2. Description of the Related Art

An enzyme is known to have a three-dimensional protein structure that is liable to change by heat or in a certain environment and lose its inherent function. Various methods have been investigated to treat an enzyme or a protein in a stable manner. In one of the methods, an enzyme or a protein is supported by a solid surface. For example, an immobilized enzyme is put into practical use.

For example, an enzyme is immobilized on silica prepared by a sol-gel method, fused quartz, a porous inorganic substance, or a porous organic polymer material. In a recent proposition, an enzyme is immobilized on a mesoporous material prepared using a detergent micelle as a template, particularly mesoporous silica. Japanese Patent Laid-Open Nos. 2000-139459 and 2002-95471 describe such a technique.

However, known techniques for immobilizing an enzyme to mesoporous silica have several problems. Specifically, mesoporous silica, such as MCM-41 or SBA-15 disclosed in Japanese Patent Laid-Open No. 2000-139459 or 2002-95471, has a small pore size reserved only for a small protein. Furthermore, mesoporous silica, such as SBA-15, has tubular pores that are longitudinally oriented in a rod-shaped particle. Thus, the tubular pores have a large aspect ratio (the ratio of the depth to the diameter of a pore). A protein or substrate molecule therefore poorly diffuses into the pores. In addition, the openings on the surface are small in number. Hence, such mesoporous silica accommodates only a smaller amount of protein.

SUMMARY OF THE INVENTION

Accordingly, the present invention provides a rod-shaped particle including a plurality of mesopores that crosses the major axis of the rod-shaped particle and that is loaded with a biological substance.

The present invention also provides a sensor for detecting a specimen. The sensor includes a rod-shaped particle including a mesopore that crosses the major axis of the rod-shaped particle and that is loaded with a biological substance, and an electrode. The sensor detects an electrical output signal generated by a reaction between the specimen and the biological substance supported by the mesopore.

The present invention also provides a method for detecting a specimen, which includes the steps of providing a sensor including a rod-shaped particle having a mesopore that crosses the major axis of the rod-shaped particle and that is loaded with a biological substance, subjecting a fluid containing a specimen to analysis by means of the sensor, and detecting an output signal generated by a reaction between the biological substance and the specimen.

The present invention provides a particle that has a small aspect ratio and that has a mesopore for immobilizing a large amount of biological substance. A particle according to the present invention can increase the sensitivity of a biosensor including the particle.

Further features of the present invention will become apparent from the following description of exemplary embodiments (with reference to the attached drawings).

DESCRIPTION OF THE EMBODIMENTS

A porous material used in the present invention will be described below.

Figure 1A:
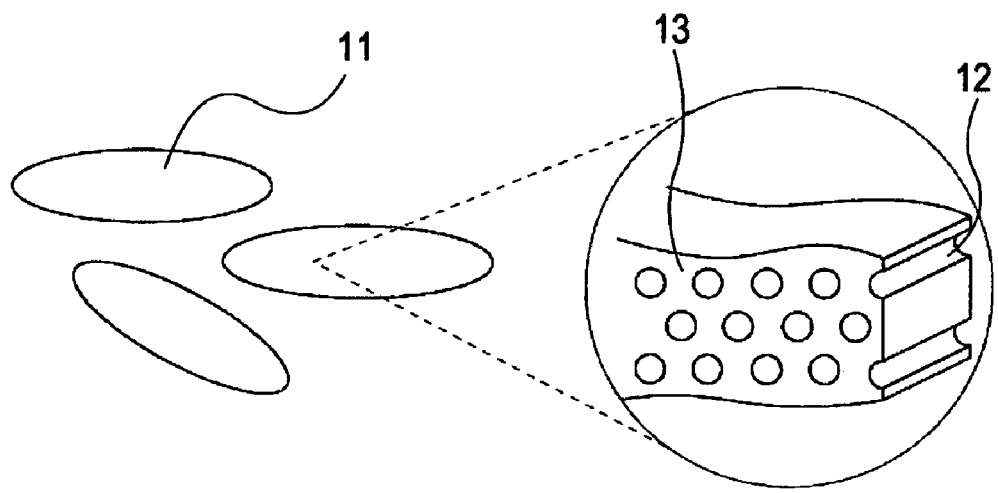
FIG. 1A and FIG. 1B are schematic views of a minor-axis-orientated mesoporous material according to an embodiment of the present invention.

FIG. 1A is a schematic view of a rod-shaped particle 11 having mesopores 12 that cross the major axis of the particle 11 according to the present invention. The term "mesopore that crosses the major axis of the rod-shaped particle" or "minor-axis-oriented" as used herein refers to the structure illustrated in FIG. 1A and FIG. 1B.

The tubular mesopores 12 are arranged parallel to the minor axis of the rod-shaped structure 11. The tubular mesopores 12 are typically arranged in a honeycomb pattern 13. In a mesoporous material according to the present invention, tubular mesopores may be arranged in any pattern substantially parallel to the minor axis of the rod-shaped structure. For example, tubular mesopores may be arranged in a grid pattern.

Figure 1B:
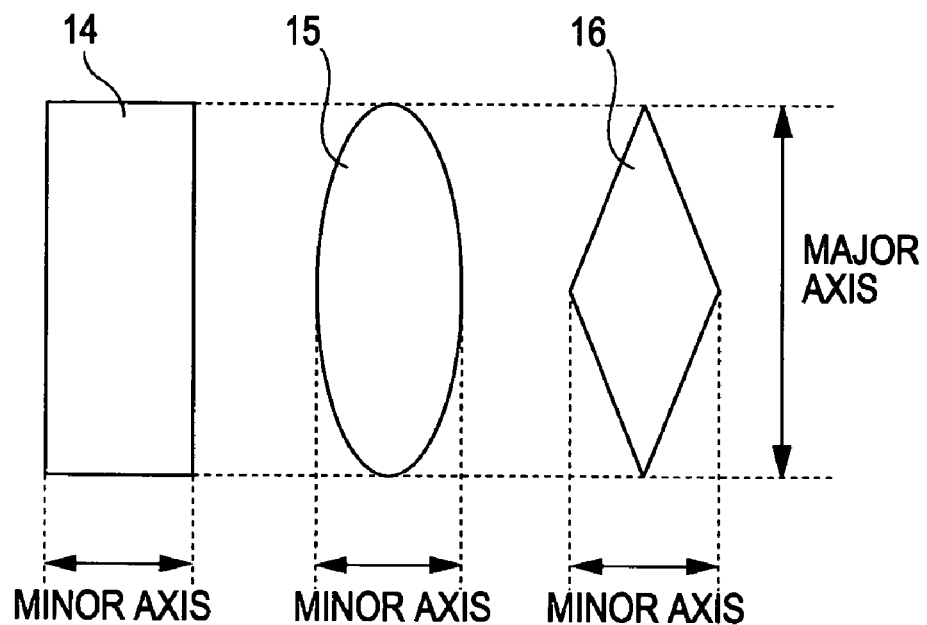

The term "rod-shaped structure" as used herein refers to those illustrated in FIG. 1A and FIG. 1B. The rod-shaped structure 11 has the minor axis having a length of 150 nm to 500 nm and the major axis having a length of 0.5 μm to 2 μm, as determined with an electron microscope. As shown in FIG.

1B, the rod-shaped structure 11 may have a longitudinal section of an ellipse, such as ellipse 15, or a polygon, such as rectangle 14 or rhombus 16.

The term "mesopore" as used herein refers to a pore having a diameter of 2 nm to 50 nm, as defined by IUPAC. The mesopore 12 can have a diameter of 10 nm to 30 nm. Within this range, an enzyme can stably be supported by the side wall of the mesopore 12 owing to the interaction between the enzyme and the side wall. The mesopore 12 can have a length 10 to 30 times the pore diameter thereof. Since known mesopores have a larger length, they are insufficiently loaded with an enzyme. By contrast, a particle according to the present invention has a smaller aspect ratio and can be loaded with a tremendously larger amount of enzyme than known mesoporous particles.

A mesopore in a mesoporous particle is formed by a detergent molecular assembly (micelle). Under a certain condition, micelles are formed of the same number of associated molecules. The resulting mesopores therefore have the same shape. While a micelle is known to be spherical, tubular, or laminar, a micelle for forming a mesoporous material according to the present invention is basically tubular. Tubular micelles may be connected to one another or may be separated from one another.

In a mesoporous material for use in the present invention, the pore wall of the porous material may be formed of any material, provided that the material for forming the pore wall has the pore structure described above. Examples of the material for forming the pore wall include titanium oxide, tin oxide, and silicon oxide. The material for forming the pore wall can be a material containing silicon and can be silica. The material for forming the pore wall may be an organic-silica hybrid material composed of an organic group having at least one carbon atom, at least two silicon atoms bound to at least two atoms of the organic group, and at least one oxygen atom bound to any of the silicon atoms.

A method for preparing a mesoporous material having a small aspect ratio using a detergent micelle as a template may be found in Journal of the American Chemical Society, 126, 7740. However, a method for preparing a mesoporous material for use in the present invention is not limited to this method and may be any method that can prepare a mesoporous material having the characteristics described above.

By way of example, a method for synthesizing a minor-axis-orientated mesoporous silica by a sol-gel method is described below.

A reactant solution contains a detergent, an organic molecule, and a raw material for a mesoporous material, such as a metal alkoxide. Depending on a material for forming a pore wall, the adequate amount of hydrolytic catalyst such as an acid may be added to the reactant solution.

The raw material for a mesoporous material may be a halide, a chalcogenide, or a metal alkoxide. For example, when the pore wall is to be formed of silica, the raw material for a mesoporous material may be a metal alkoxide, such as tetraethoxysilane or tetramethoxysilane. A silica source other than a metal alkoxide may also be used in the present invention.

The detergent may be a nonionic detergent, such as a block copolymer containing polyethylene oxide as a hydrophilic group. However, any detergent may be used, provided that the detergent provides a target structure.

The orientation of tubular mesopores along the minor axis is controlled by the type and the amount of the organic molecule. For example, a rod-shaped mesoporous silica having a minor-axis-orientated pore structure can be synthesized using n-decane.

The acid catalyst may be a common acid, such as hydrochloric acid or nitric acid.

Such a reactant solution is allowed to react under hydrothermal conditions to form a mesoporous material according to the present invention. The reaction temperature may be 80° C. to 150° C. The reaction time may be several hours to several days. The reaction temperature and the reaction time are optimized appropriately.

A mesoporous material thus prepared is washed in pure water and is air-dried to yield an inorganic-organic composite powder material containing detergent micelles in pores as templates. The detergent micelles are removed from the inorganic-organic composite powder material to yield a minor-axis-orientated mesoporous material having a small aspect ratio for use in the present invention. The detergent may be removed by any method, provided that the detergent can be removed without destroying the pore structure.

In the most commonly used method for removing the detergent, a mesoporous material is fired in an atmosphere containing oxygen. For example, a mesoporous material can be fired in the air at 550° C. for 10 hours to completely remove the detergent without causing significant destruction of the mesopore structure. The firing temperature and the firing time are optimized according to the material that forms a pore wall and the type of detergent.

A mesoporous powder sample thus synthesized is subjected to nitrogen adsorption and desorption to determine the pore size. A mesoporous material according to the present invention may have a substantially uniform pore size distribution. The "substantially uniform pore size distribution" as used herein means that the pore size distribution has a single maximum, as determined by the Berrett-Joyner-Halenda (BJH) method in the nitrogen adsorption, and that at least 60% of the mesopores are within a pore size distribution width of 10 nm. The pore size can be changed by the type of detergent described below.

The periodic structure of mesopores can be determined by an X-ray diffraction (XRD) analysis. In a mesoporous material according to the present invention, at least one diffraction peak may exist at an angle corresponding to a periodic structure of at least 1 nm in an X-ray diffraction analysis.

A layer of a material that is different from that of the pore wall, for example, an organic substance layer or an inorganic oxide layer may be formed on the surface of a mesopore in a mesoporous material for use in the present invention.

A typical example of the organic substance is a silane coupling agent. A typical example of the inorganic oxide is an aqueous solution of a metallic salt containing an oxide-forming metal.

A silane coupling agent has a general formula of R—Si—$X_3$ and has at least two functional groups in the molecule. The X denotes a moiety that can react with the surface of a porous inorganic material. For example, Sol-Gel Science, 1989, 662 describes mesoporous silica. This document discloses that hydrogen of a silanol group on the pore surface is replaced by an organic silicon group to form a Si—O—Si—R bond, thus forming a layer of an organic substance R on the pore surface.

The X is known to be a chloro group, an alkoxy group, an acetoxy group, an isopropenoxy group, or an amino group. The X in the present invention is not limited to these. The X may not only be a trifunctional group, but also a bifunctional group or a monofunctional group, provided that the X can react with a pore surface to form the R layer.

The R denotes an organic group and can be, but not limited to, an amino group, a carboxyl group, or a maleimide group.

A method for modifying a pore surface with an aqueous solution of a metallic salt containing an oxide-forming metal is described below. The "oxide" as used herein refers to a compound having at least one bond between an element such as a metal and oxygen. Examples of a metal that can form an oxide layer include titanium, aluminum, zirconium, and tin. For example, mesoporous silica can be treated with aqueous zirconium oxynitrate to form a zirconium oxide layer on the surface. The metallic salt may be composed of any metal, provided that an aqueous solution of the metallic salt can form a metal oxide layer on a pore surface.

A material containing an immobilized biological substance according to the present invention is described below.

Figure 2:
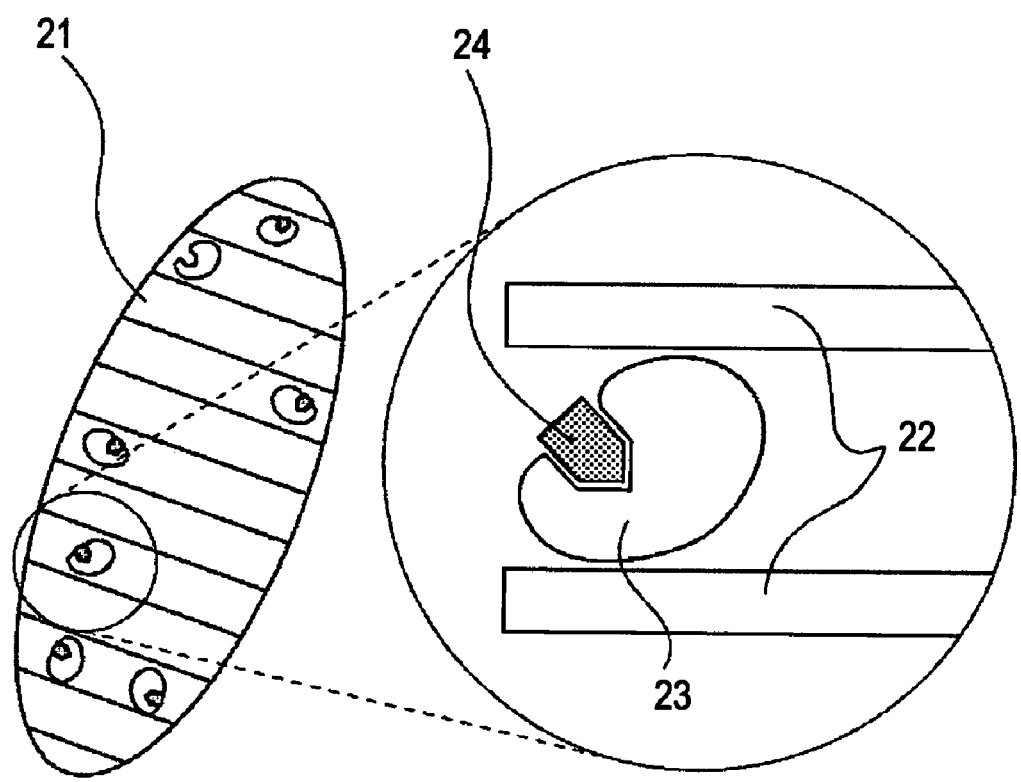
FIG. 2 is a schematic view of a stabilized enzyme in a minor-axis-orientated mesoporous material synthesized in Example 1 of the present invention.

FIG. 2 is a schematic view of a material containing an immobilized biological substance according to an example of the present invention. A minor-axis-orientated structure 21 includes pore walls 22 formed of a mesoporous material. A biological substance 23, such as a protein or an enzyme, is bound to a substrate or a fragment 24. The substrate can specifically be bound to the biological substance 23, and the fragment can specifically react with the biological substance 23.

An anchor (not shown) may connect the biological substance 23 to a pore wall 22. The anchor may have an effect of reducing a large structural change of the biological substance to hold it stably. However, the anchor is not an essential component.

The anchor can be composed of substantially the same component as the mesoporous material.

The anchor can have the following functional group to be bound particularly to a biological substance:

a hydroxyl group, an amide group, an amino group, a pyridine group, a urea group, a urethane group, a carboxyl group, a phenol group, an azo group, a hydroxyl group, a maleimide group, a silane derivative, or an aminoalkylene group.

Each pore accommodates at least one biological substance. Thus, the pores must have a size appropriate to immobilize a biological substance. The pore size depends on the size of a biological substance to be immobilized.

When a biological substance is immobilized in a pore, the biological substance can be adsorbed on an inner surface of the pore by electrostatic bonding. A biological substance may also be held in a pore by a noncovalent bonding, such as van der Waals forces, hydrogen bonding, or ionic bonding.

Examples of a biological substance to be immobilized include an antigen, an antibody, a protein, and an enzyme molecule. A biological substance to be immobilized may also be a fragment containing an active site, such as a Fab antibody. A biological substance may be an extract of an animal, a plant, or a microorganism. If desired, the extract may be cut into pieces. A biological substance may also be synthesized by genetic engineering or chemical reactions.

The present invention will be described in detail with reference to examples. However, the present invention is not limited to these examples.

EXAMPLE 1

In the present example, a rod-shaped mesoporous silica was manufactured. Substantially uniform tubular mesopores were arranged parallel to the minor axis of the rod-shaped structure. The rod-shaped mesoporous silica was used to immobilize an enzyme.

2.40 g of triblock copolymer ($EO_{20}PO_{70}EO_{20}$; $HO(CH_2CH_2O)20(CH_2CH(CH_3)O)70(CH_2CH_2O)_{20}H$), which is a nonionic detergent, was dissolved in 76.5 ml of pure water. 7.5 ml of 36% by weight concentrated hydrochloric acid was added to the solution. The solution was stirred at room temperature for 30 min. Then, 13.9 g of n-decane was added to the solution. The solution was stirred at room temperature for two hours. 0.027 g of $NH_4F$, which serves as a hydrolytic catalyst, and 5.10 g of tetraethoxysilane (TEOS) were added to the solution to prepare a precursor solution, which had a final composition (molar ratio) of TEOS:HCl:$EO_{20}PO_{70}EO_{20}$:$NH_4F$:n-decane:$H_2O$=0.25:0.9:0.004: 0.007:1:42.9.

The precursor solution was stirred at 40° C. for 20 hours and was allowed to react at 100° C. for 48 hours. The resulting white precipitate was sufficiently washed in pure water and was dried in a vacuum.

The resulting powder sample was fired in the air at 550° C. to remove the detergent from the pores and thereby form hollow pores. The removal of organic substances, including the detergent, was checked by an infrared absorption spectrum.

Figure 3:
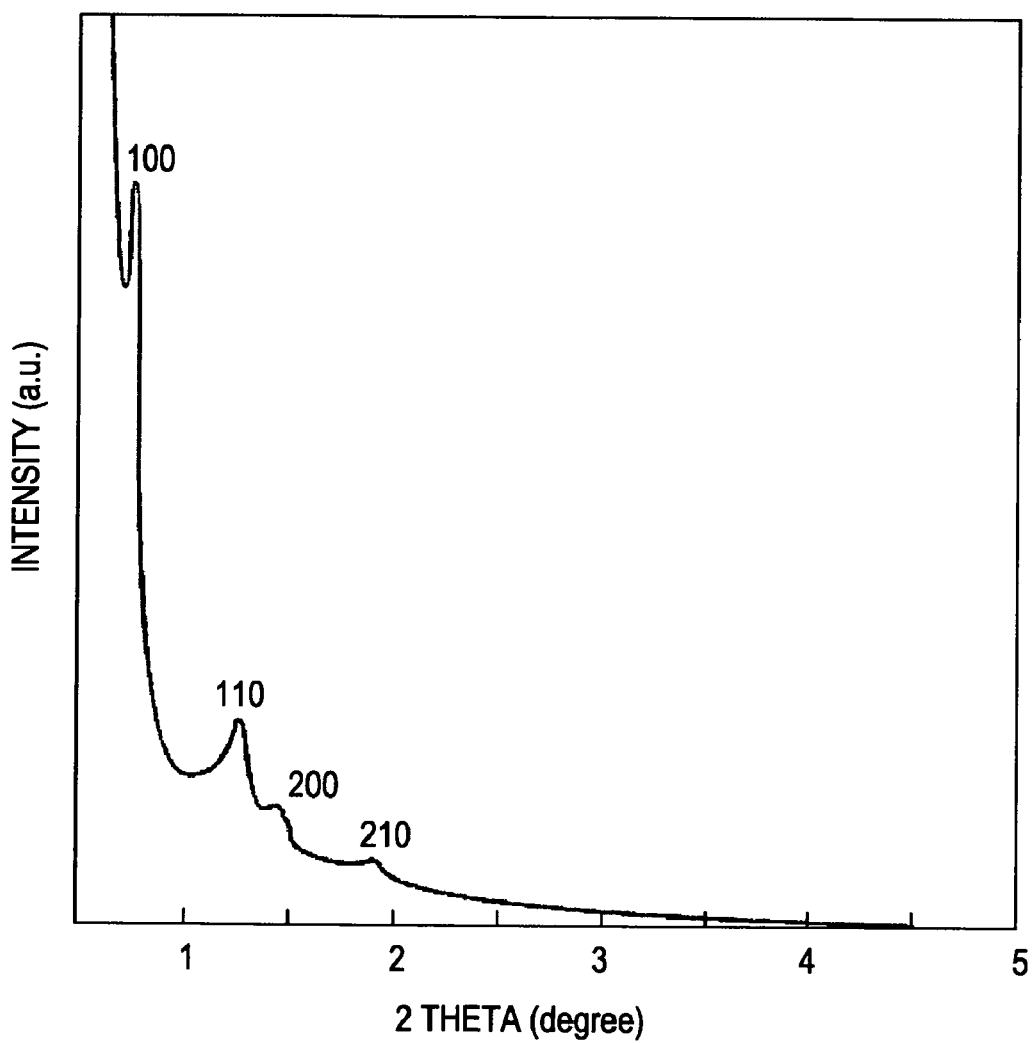
FIG. 3 is a graph of an X-ray diffraction of a minor-axis-orientated mesoporous material according to an embodiment of the present invention.

FIG. 3 illustrates an X-ray diffraction chart of the mesoporous silica powder thus synthesized. Diffraction peaks were assigned to (100), (110), (200), and (210) planes of a hexagonal structure having an interplanar spacing of 11.7 nm. This result showed that the pores of the mesoporous silica were arranged hexagonally with high regularity.

The nitrogen adsorption and desorption of the mesoporous silica at 77 K showed an adsorption isotherm of type IV according to the IUPAC classification. The mesoporous silica had a specific surface area of 700 $m^2/g$ and a pore volume of 1.88 ml/g, as determined by a Brunauer-Emmett-Teller (BET) equation. The pore size distribution of the mesoporous silica was calculated from the adsorption isotherm by the BJH method. The mesoporous silica had a narrow pore size distribution having a single peak at 14.3 nm. 90% of the pores were within a pore size distribution width of 10 nm.

Figure 4:
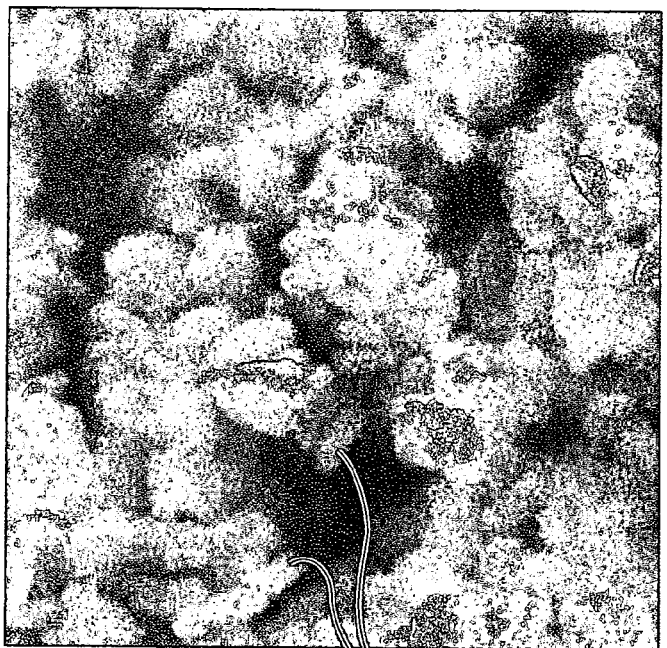
FIG. 4 is a scanning electron microscope photograph of a minor-axis-orientated mesoporous material according to an embodiment of the present invention.
Figure 5:
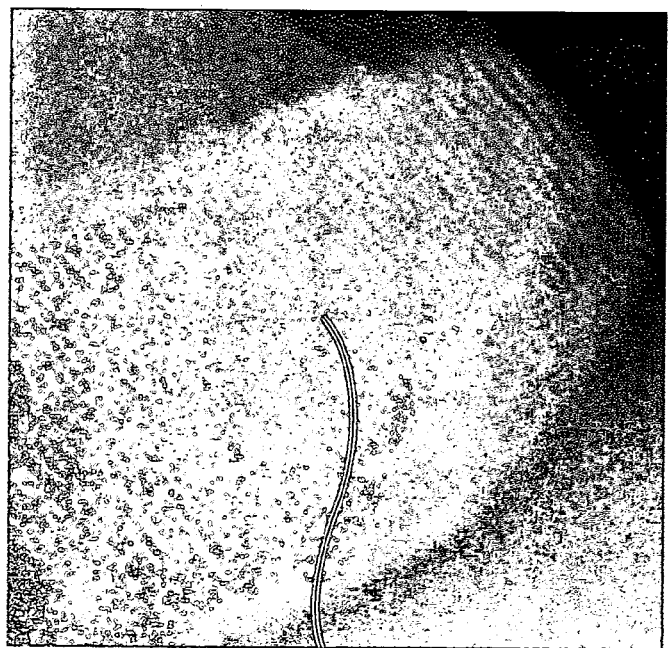
FIG. 5 is a highly magnified scanning electron microscope photograph of a minor-axis-orientated mesoporous material according to an embodiment of the present invention.
Figure 6:
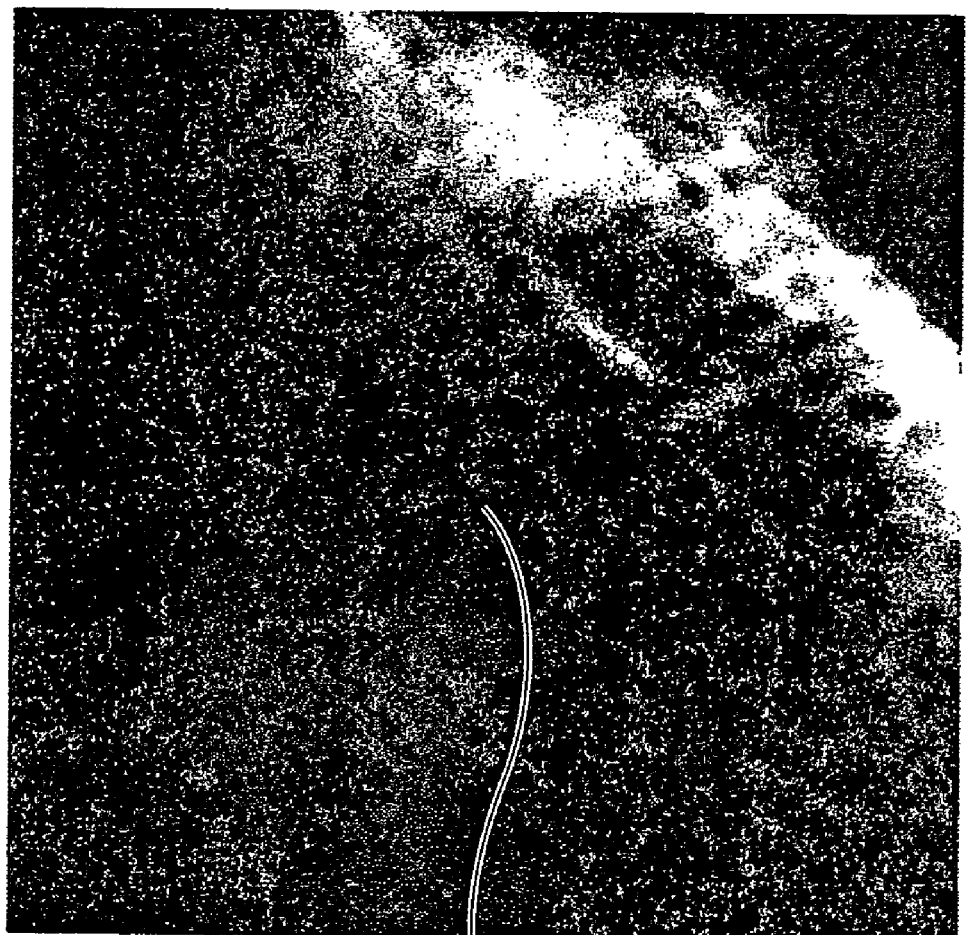
FIG. 6 is a highly magnified scanning electron microscope photograph of a cross section of the minor-axis-orientated mesoporous material illustrated in FIG. 4.

As illustrated in FIG. 4, a scanning electron microscope (SEM) photograph showed that the mesoporous silica 11 had a rod-shaped structure. As illustrated in FIG. 5, a highly magnified SEM photograph showed that tubular mesopores 12 having a diameter of 14 nm were orientated parallel to the minor axis of the mesoporous silica. As illustrated in FIG. 6, in a cross section of the minor-axis-orientated mesoporous material, relatively uniform tubular mesopores 12 were arranged in a honeycomb pattern. The mesopore structure was not destroyed by an electron beam during the observation.

Then, horseradish peroxidase (hereinafter referred to as HRP, average diameter=4.8 nm, isoelectric point (IEP)=7.8), which is an oxidoreductase, was immobilized in the mesopores of the mesoporous silica, and was analyzed for thermal stability and resistance to an organic solvent.

5 mg/ml HRP solution was prepared using 5 mM phosphate buffer (pH=7.0). 10 mg of the mesoporous silica was added to 1 ml of this enzyme solution. The mixture solution was stirred at 4° C. for 20 hours in a shaker so that HRP was adsorbed on the mesopores. After the completion of the adsorption, the mixture solution was centrifuged at 20000 g at 4° C. for 10 min. A precipitate of HRP-mesoporous silica was washed in pure water three times. The enzyme solution and the supernatant were analyzed for UV-Vis absorbance. An absorption maximum of HRP at 403 nm was used to calculate the amount of HRP adsorbed on the mesoporous silica on the basis of the change in the HRP concentration by the adsorption. Then, the mesoporous silica containing immobilized enzyme molecules was freeze-dried in a vacuum for 10 hours to produce a powder sample. The amount of adsorbed HRP was as high as 252 mg per gram of the mesoporous silica. The amount of adsorbed HRP varied with the pH of the phosphate buffer. This indicated that HRP was immobilized on the mesoporous silica by an electrostatic interaction.

The adsorption of HRP molecules on the mesopores was confirmed by a decrease in nitrogen adsorption on the mesoporous silica.

The mesoporous silica containing immobilized HRP was analyzed for resistance to an organic solvent in an oxidation reaction in toluene and thermal stability in an oxidation reaction of phenol.

The activity of HRP immobilized on the mesoporous silica in an organic solvent was evaluated in an oxidation reaction of 1,2-diaminobenzene in toluene using tert-butyl hydroperoxide as an oxidizing agent. 8 ml of anhydrous toluene containing 50 mM 1,2-diaminobenzene was mixed with 2 ml of 1.1 M tert-butyl hydroperoxide in n-decane. 10 mg of the mesoporous silica containing immobilized HRP was added to 1 ml of this mixture solution to initiate a reaction at 37° C. The activity of HRP in toluene was determined by measuring the absorbance at 470 nm of 1,2-dinitrobenzene, which was produced by the oxidation of 1,2-diaminobenzene, as a function of time.

Figure 7:
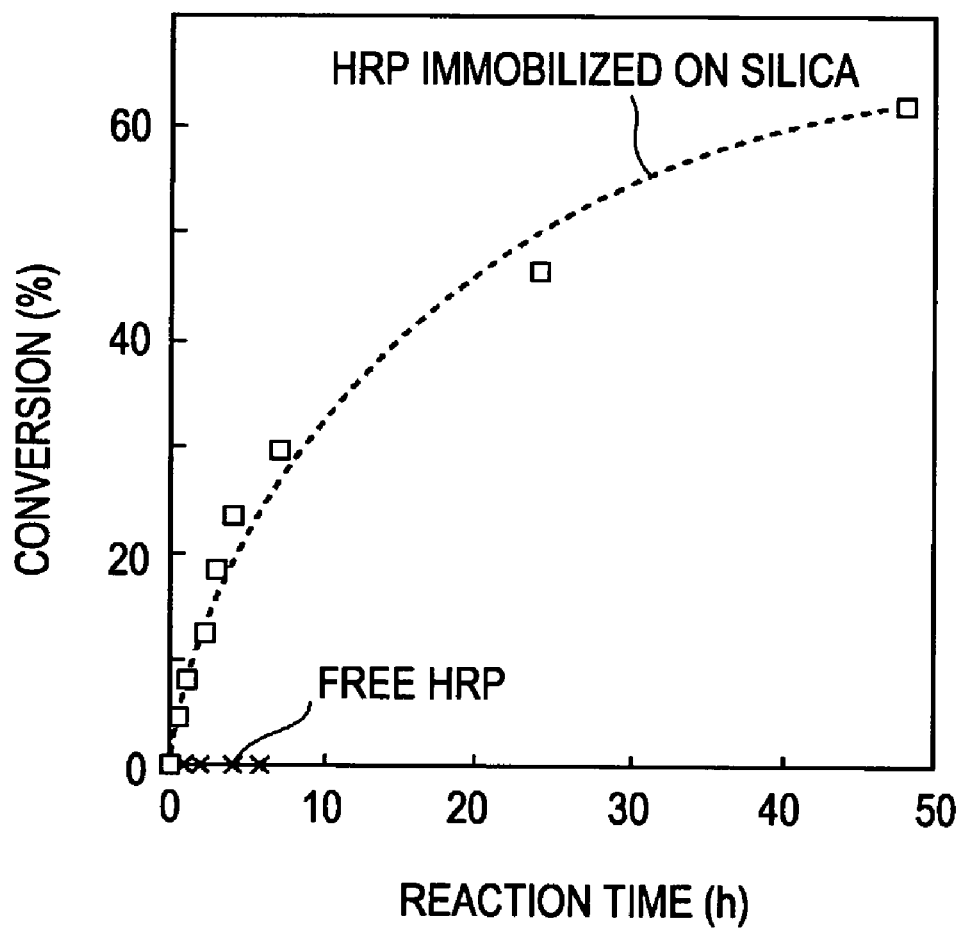
FIG. 7 is a graph of the conversion as a function of time in an enzymatic reaction of horseradish peroxidase in toluene. The horseradish peroxidase is immobilized in the minor-axis-orientated mesoporous material synthesized in Example 1 of the present invention.

As a comparative test, the oxidation reaction was performed with 0.5 mg of HRP, and the absorbance at 470 nm was measured. FIG. 7 shows the result. In the presence of HRP alone (free HRP), the oxidation reaction in toluene was not observed. By contrast, HRP immobilized on the mesoporous silica exhibited a very high activity. HRP may degenerate immediately after HRP was added to toluene. Hence, HRP immobilized on the mesoporous silica exhibited high stability.

Figure 8:
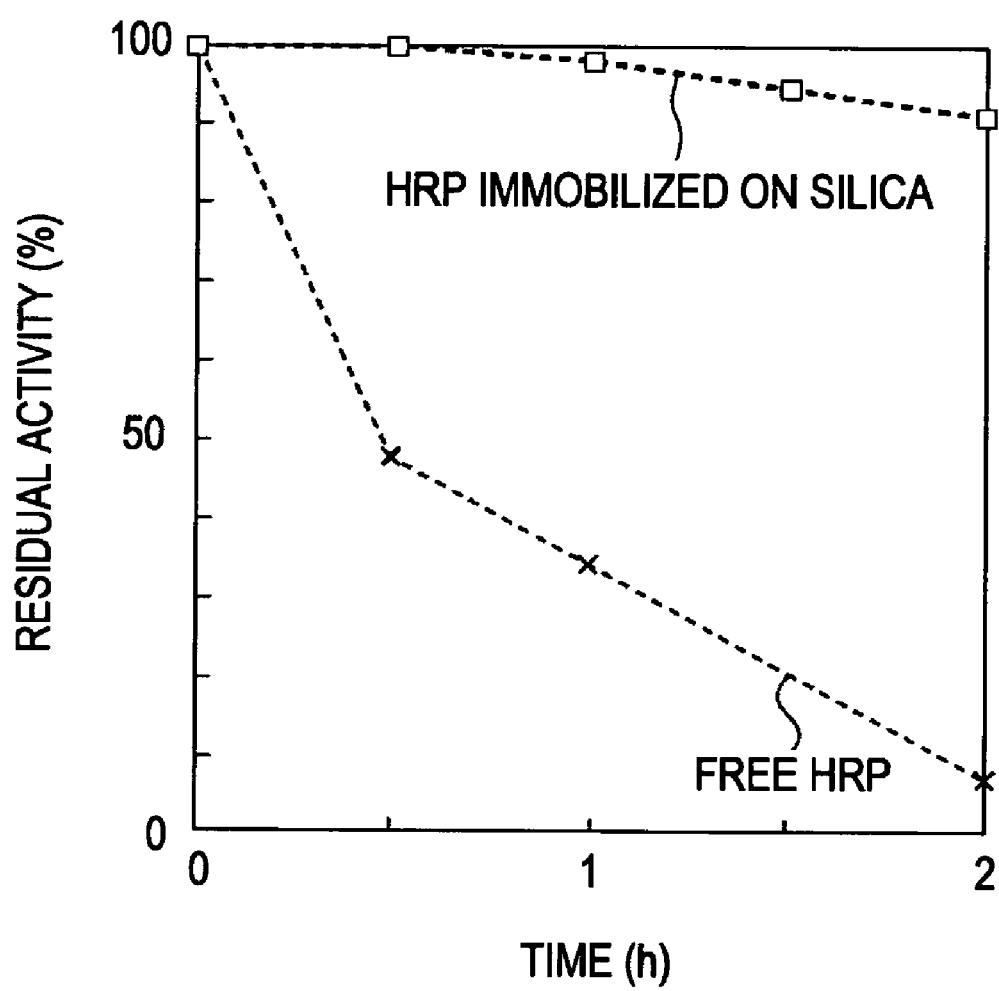
FIG. 8 is a graph of the relative activity of horseradish peroxidase as a function of heat treatment time at 70° C. The horseradish peroxidase is immobilized in the minor-axis-orientated mesoporous material synthesized in Example 1 of the present invention.

Mesoporous silica containing immobilized HRP and free HRP were heat-treated at 70° C. for 0 to 2 hours in a phosphate buffer. FIG. 8 illustrates the residual activities of the HRPs. The thermal stability of HRP immobilized on the mesoporous silica was determined by measuring the oxidative decomposition rate of phenol. The amount of phenol was measured by a 4-aminoantipyrine colorimetric method.

400 μl of 50 mM sodium acetate buffer solution (pH=4.0) was added to 10 mg of the mesoporous silica containing immobilized HRP. The mixture was heated at 70° C. for 30, 60, 90, and 120 min. After centrifugation, the mesoporous silica containing immobilized HRP was washed in pure water two times. 400 μl of 50 mM Tris-HCl (tris(hydroxymethyl) aminomethane hydrochloride) buffer solution (pH=7.5), 8 μl of 5000 ppm aqueous phenol, and 2 μl of 30% hydrogen peroxide solution were added to the mesoporous silica containing immobilized HRP. The mixture was allowed to react at 37° C. for 30 min. After centrifugation, 150 μl of supernatant liquid, and 150 μl of 1% hexacyanoferrate and 300 μl of 1% 4-aminoantipyrine each dissolved in 1 M aqueous solution of glycine (pH=9.6) were added to the mixture with stirring. The absorbance of the mixture was immediately measured in the vicinity of 500 nm.

As illustrated in FIG. 8, the activity of free HRP decreased nearly one-half after the heat treatment at 70° C. for 30 min and to nearly one-tenth of the initial value after two hours of heat treatment. By contrast, HRP immobilized on the mesoporous silica exhibited excellent thermal stability and had an activity of more than 90% of the initial value even after two hours of heat treatment.

Figure 9:
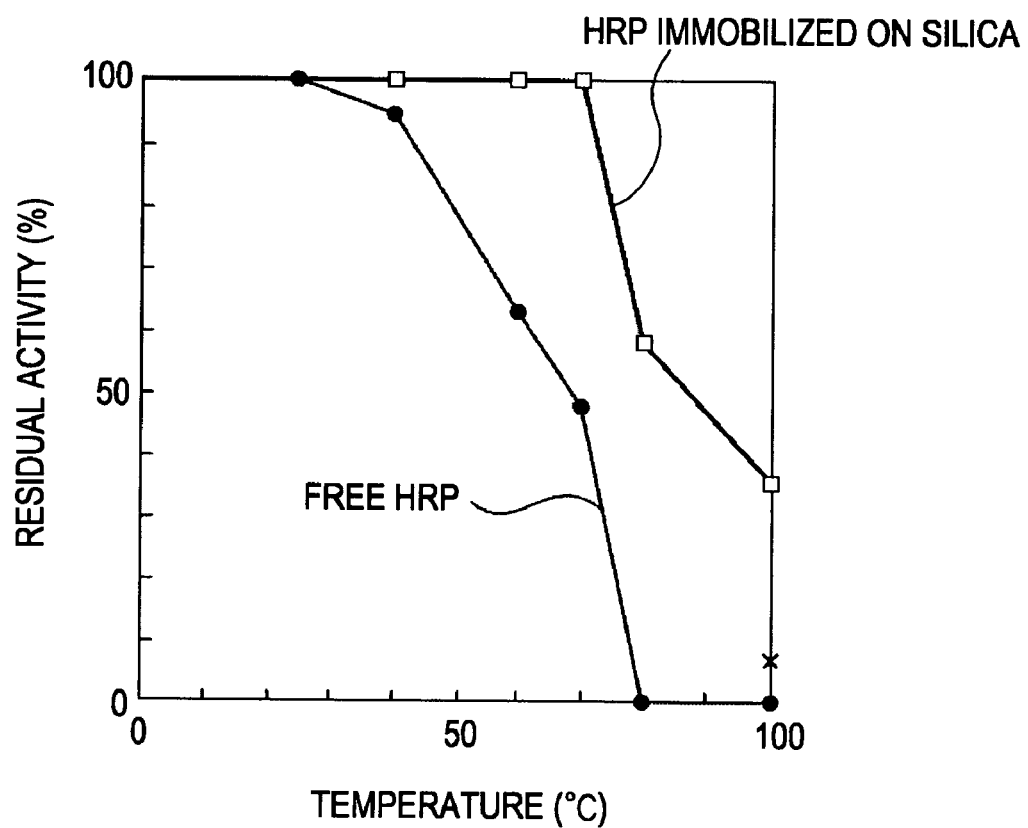
FIG. 9 is a graph of the relative activity of horseradish peroxidase as a function of temperature. The horseradish peroxidase is immobilized in the minor-axis-orientated mesoporous material synthesized in Example 1 of the present invention and is heat-treated at each temperature for 30 min.

FIG. 9 illustrates the activity of HRP as a function of temperature in the oxidation reaction of phenol. Free HRP and immobilized HRP were heat-treated at a temperature of 25° C. to 100° C. for 30 min. While the residual activity of the free HRP was 0% at 80° C., that of the HRP immobilized on the mesoporous silica held more than 50% of its initial value at the same temperature. Furthermore, the residual activity of the HRP immobilized on the mesoporous silica held nearly 40% of its initial value at 100° C.

COMPARATIVE EXAMPLE 1

SBA-15 was synthesized and was analyzed for adsorption of HRP and stability in an organic solvent of HRP immobilized in SBA-15. SBA-15 includes longitudinally tubular pores in its rod-shaped particle. The synthesis method of SBA-15 may be found in Science, 279, 548.

The X-ray diffraction of the SBA-15 showed a diffraction peak assigned to a (100) plane of a hexagonal structure having an interplanar spacing of 9.8 nm. The SBA-15 had a specific surface area of 800 $m^2/g$ and a pore size of 7.4 nm, as determined from a nitrogen adsorption isotherm.

A HRP adsorption experiment with the SBA-15 was performed as in Example 1. The amount of HRP adsorbed on the SBA-15 was 25 mg/g, which was about one-tenth of the amount of HRP adsorbed on the minor-axis-orientated mesoporous silica according to the present invention. Furthermore, the nitrogen adsorption isotherm after the HRP adsorption showed that the pore volume of the SBA-15 was not changed by the HRP adsorption, indicating little HRP was adsorbed in the pores of the SBA-15. Considering that the average diameter of HRP was 4.8 nm and the SBA-15 had a pore size of 7.4 nm, the pore opening may be too small for HRP to enter the pore. By contrast, HRP adsorption in the minor-axis-orientated mesoporous silica reached a saturation level in a short time.

The resistance of HRP immobilized on the SBA-15 to an organic solvent was compared with that of the minor-axis-orientated mesoporous silica according to the present invention. A minute quantity of HRP immobilized on the SBA-15 had some activity. A reaction product 1,2-dinitrobenzene increased with time. However, the amount of 1,2-dinitrobenzene in the SBA-15 was less than one-tenth of that in the minor-axis-orientated mesoporous silica according to the present invention.

Because the SBA-15 includes longitudinally tubular pores in its rod-shaped particle, the tubular pores have a larger aspect ratio. Therefore, HRP or a substrate hardly diffuses from the outside to the inside or from the inside to the outside of the pore. In addition, because the number of openings on the surface is smaller, a lesser number of HRP or substrate molecules is introduced at a time. These results show that the minor-axis-oriented mesoporous silica according to the present invention can advantageously support a biological substance.

EXAMPLE 2

The surface of the minor-axis-orientated mesoporous silica prepared in Example 1 was modified with zirconium oxide. Bovine serum albumin (hereinafter referred to as BSA, diameter=7.0 nm, IEP=4.7) was immobilized on the surface and was analyzed for thermal stability.

10 g of zirconium oxynitrate dihydrate was dissolved in 90 ml of pure water at room temperature to prepare 10% by weight aqueous solution of zirconium oxynitrate. The minor-axis-orientated mesoporous silica synthesized in Example 1 was dipped in this solution for 20 hours. Then, the supernatant was removed by centrifugation. The minor-axis-orientated mesoporous silica was washed in pure water three times and was dried at room temperature.

The X-ray diffraction of the minor-axis-orientated mesoporous silica modified with zirconium was substantially the same as that of the minor-axis-orientated mesoporous silica before modification, indicating that the periodic structure of the mesopores was not destroyed. The chemical bonding on the surface of the mesoporous silica was examined by X-ray photoelectron spectroscopy (XPS). The XPS showed a peak assigned to Zr—O, indicating the formation of a zirconium oxide layer on the surface.

BSA immobilized in the pores of the mesoporous silica modified with zirconium was allowed to react with HRP-labeled anti-BSA antibody (antigen-antibody reaction) to determine the stabilizing effect of the mesoporous silica.

5 ml of 1 mg/ml BSA dissolved in 10 mM phosphate buffer (pH=5.0) was added to 10 mg of the minor-axis-orientated mesoporous silica modified with zirconium. The mixture was stirred at 4° C. for 6 hours to immobilize BSA in the mesopores of the mesoporous silica. Then, the mesoporous silica was washed in pure water three times. BSA was not adsorbed on the minor-axis-orientated unmodified mesoporous silica.

BSA immobilized on the mesoporous silica was allowed to react with a HRP-labeled anti-BSA antibody (hereinafter referred to as HRP-antiBSA) at room temperature for a predetermined time (1 to 4 hours). The mesoporous silica containing immobilized BSA was washed in pure water several times to remove nonspecifically adsorbed HRP-antiBSA, was freeze-dried in a vacuum, and was left standing at 37° C. for a predetermined time. 400 µl of 50 mM Tris-HCl (pH=7.5), 8 µl of 5000 ppm aqueous phenol, and 2 µl of 30% hydrogen peroxide solution were added to the mesoporous silica containing immobilized BSA. The mixture was allowed to react at 37° C. for 30 min. After centrifugation, 150 µl of supernatant liquid, and 150 µl of 1% hexacyanoferrate and 300 µl of 1% 4-aminoantipyrine each dissolved in 1 M aqueous solution of glycine (pH=9.6) were added to the mixture with stirring. The absorbance of the mixture was immediately measured in the vicinity of 500 nm to determine the activity of HRP in the HRP-antiBSA specifically bound to the immobilized BSA.

Nonspecific ovalbumin (egg albumin, diameter=7.0 nm, IEP=4.9) was immobilized on the mesoporous silica by the same method as described above and was allowed to react with the anti-BSA antibody. The difference in absorbance between the mesoporous silica containing immobilized ovalbumin and the mesoporous silica containing immobilized BSA was determined by the procedure described above. The nonspecific ovalbumin had smaller HRP activity than the mesoporous silica containing immobilized BSA according to the present example. These results showed that BSA was immobilized on the mesoporous silica and that BSA immobilized on the mesoporous silica effectively underwent an antigen-antibody reaction in the pores.

The mesoporous silica containing immobilized BSA and a common BSA powder were stored at 40° C. under dry condition for three weeks. Then, their HRP activities were measured as described above. After one week, free BSA completely lost its HRP activity. By contrast, the BSA immobilized on the mesoporous silica had 90% or more of its initial HRP activity.

EXAMPLE 3

The surface of the minor-axis-orientated mesoporous silica synthesized in Example 1 was modified with a silane coupling agent. α-amylase was covalently immobilized on the silica surface.

1.0 g of the minor-axis-orientated mesoporous silica synthesized in Example 1 was added to 50 ml of 10% (v/v) 3-aminopropyltriethoxysilane in toluene. The solution was stirred at 120° C. for 48 hours in an atmosphere of nitrogen. After the reaction completed, a precipitate was filtered, was washed with toluene, methanol, and dichloromethane, and was dried at room temperature.

1.0 g of the dry product was dissolved in 25 ml of 2.5% glutaraldehyde in a phosphate buffer (pH=6.6). The solution was stirred at room temperature for one hour. The resulting precipitate was washed in pure water at least four times and was dried at room temperature.

The X-ray diffraction of the minor-axis-orientated mesoporous silica modified with glutaraldehyde was substantially the same as that of the minor-axis-orientated mesoporous silica before modification, indicating that the mesoporous structure was not destroyed. The FT-IR spectroscopy of the silica surface showed peaks assigned to R—CH=N, C=O, and —CHO, indicating that $Si(CH_2)_3N=CH(CH_2)_3CHO$ was covalently bonded to the silica surface.

Then, α-amylase was immobilized in the pores of the modified mesoporous silica. A hydrolysis reaction of starch to yield maltose was used to determine the stabilizing effect of the modified mesoporous silica.

0.2 g of the minor-axis-orientated modified mesoporous silica was added to 1 ml of 1 mg/ml α-amylase in 50 mM phosphate buffer (pH=6.0). The minor-axis-orientated modified mesoporous silica was impregnated with the mixture solution at 4° C. for 20 hours in a shaker. After the completion of the reaction, the minor-axis-orientated modified mesoporous silica was filtered and was washed in pure water three times. The enzyme solution and the supernatant were analyzed for UV-Vis absorbance. An absorption maximum of α-amylase at 280 nm was used to calculate the amount of α-amylase adsorbed on the modified mesoporous silica on the basis of the change in the HRP concentration by the adsorption. The amount of adsorbed α-amylase was as high as 140 mg/g. α-amylase was not adsorbed on the minor-axis-orientated unmodified mesoporous silica under the same conditions. Hence, α-amylase was immobilized on the silica surface by the bonding between —CHO on the silica surface and —NH$_2$ of α-amylase.

The mesoporous silica containing immobilized α-amylase and free α-amylase were heat-treated at 25° C. to 70° C. in a sodium acetate buffer and were analyzed for the enzyme activity.

400 µl of 50 mM sodium acetate buffer (pH=5.0) was added to 10 mg of the mesoporous silica containing immobilized α-amylase. The mixture was heat-treated at 25° C. to 70° C. for 30 min. After centrifugation, the mesoporous silica containing immobilized α-amylase was washed in pure water two times. 300 µl of 0.125% soluble starch in 50 mM sodium acetate buffer was allowed to react with the mesoporous silica containing immobilized α-amylase at 40° C. for 15 min. After the reaction was terminated, 1 ml of 0.5 N acetic acid and 3 ml of iodine-potassium (0.015% iodine-0.15% potassium iodide) solution were added to a supernatant obtained by centrifugation of the reaction product. The mixture was sufficiently stirred and was analyzed for an absorption maximum at 700 nm. While the free α-amylase had a relative activity of 20% after heat-treatment at 60° C. for 30 min, α-amylase immobilized on the minor-axis-orientated mesoporous silica had a relative activity of 90% or more under the same conditions. This demonstrates the stabilizing effect of the minor-axis-orientated mesoporous silica.

EXAMPLE 4

Goat IgG Fab fragments (diameter=about 12 nm) were immobilized in the pores of the minor-axis-orientated mesoporous silica synthesized in Example 1. The stability of the goat IgG Fab fragments was examined in an antigen-antibody specific binding reaction.

10 ml of 1 mg/ml Fab fragments of anti-mouse immunoglobulin G (IgG) in 10 mM phosphate buffer was added to 10 mg of the minor-axis-orientated mesoporous silica synthesized in Example 1 or 10 mg of SBA-15 used in Comparative Example 1. Each solution was stirred at 4° C. for six hours to immobilize the antibody in the mesopores of the mesoporous silica. The amount of adsorbed Fab fragments was measured with a UV-Vis absorptiometer at 280 nm. About 150 mg/ml of Fab fragments were adsorbed on the minor-axis-orientated mesoporous silica. However, no adsorption was observed in the SBA-15.

Then, the minor-axis-orientated mesoporous silica was washed in pure water three times. Fab fragments immobilized on the minor-axis-orientated mesoporous silica was allowed to react with a HRP-labeled mouse IgG antibody (hereinafter referred to as HRP-IgG) solution at room temperature for a predetermined time (1 to 4 hours). The minor-axis-orientated mesoporous silica containing immobilized antigens and antibodies was washed in pure water several times to remove nonspecifically adsorbed HRP-IgG, and was freeze-dried in a vacuum, and was left standing at 37° C. for a predetermined time. 400 μl of 50 mM Tris-HCl (pH=7.5), 8 μl of 5000 ppm aqueous phenol, and 2 μl of 30% hydrogen peroxide solution were added to the minor-axis-orientated mesoporous silica containing immobilized antigens and antibodies. The mixture was allowed to react at 37° C. for 30 min. After centrifugation, 150 μl of supernatant liquid, and 150 μl of 1% hexacyanoferrate and 300 μl of 1% 4-aminoantipyrine each dissolved in 1 M aqueous solution of glycine (pH=9.6) were added to the mixture with stirring. The absorbance of the mixture was immediately measured in the vicinity of 500 nm to determine the activity of HRP in the HRP-IgG specifically bound to the immobilized Fab fragments.

IgG Fab fragments other than the anti-mouse IgG Fab fragments were immobilized on the minor-axis-orientated mesoporous silica in the same way as described above. Difference in absorbance between the Fab fragments that can be specifically bound to the mouse IgG antibody and the nonspecific Fab fragments was determined. The nonspecific IgG Fab fragments other than the anti-mouse IgG Fab fragments had a HRP activity lower than that of the anti-mouse IgG Fab fragments immobilized on the mesoporous silica according to the present example. These results showed that an active substance having a diameter of 12 nm was immobilized in the minor-axis-orientated mesoporous silica and that the active substance thus immobilized on the mesoporous silica effectively underwent an antigen-antibody reaction.

The mesoporous silica containing immobilized anti-mouse IgG Fab fragments and a free Fab powder were stored at 37° C. under dry condition for three weeks. Then, their HRP activities were determined in an antigen-antibody reaction. After being stored for 12 hours, the free Fab powder completely lost its HRP activity. By contrast, the Fab fragments immobilized on the minor-axis-orientated mesoporous silica had 80% or more of its initial HRP activity in the antigen-antibody reaction even after two weeks.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2005-375172 filed Dec. 27, 2005, which is hereby incorporated by reference herein in its entirety.

What is claimed is:

1. A rod-shaped particle, comprising:
a plurality of mesopores that is arranged parallel to the minor axis of the rod-shaped particle, the plurality of mesopores being loaded with a biological substance,
wherein the major axis of the rod-shaped particle has a length of 0.5 μm to 2 μm, and the minor axis of the rod-shaped particle has a length of 150 nm to 500 nm.

2. The particle according to claim 1, wherein each of the plurality of mesopores has a length 10 to 30 times the pore diameter thereof.

3. The particle according to claim 1, wherein each of the plurality of mesopores has a pore diameter of 10 to 30 nm.

4. The particle according to claim 1, wherein the plurality of mesopores is arranged in a honeycomb pattern.

5. The particle according to claim 1, wherein the biological substance is a protein.

6. The particle according to claim 1, wherein the plurality of mesopores has a pore size distribution having a single maximum diameter, as determined by nitrogen gas adsorption, and at least 60% of the plurality of mesopores is within 10 nm or less from the single maximum diameter.

7. The particle according to claim 1, wherein the plurality of mesopores has at least one diffraction peak at an angle corresponding to a periodic structure of at least 1 nm in an X-ray diffraction analysis.

8. A sensor for detecting a specimen, comprising:
the particle according to claim 1; and
an electrode,
wherein the sensor detects an electrical output signal generated by a reaction between the specimen and the biological substance loaded in the plurality of mesopores.

9. A method for detecting a specimen, comprising the steps of:
providing a sensor comprising the particle according to claim 1;
subjecting a fluid containing the specimen to analysis by means of the sensor; and
detecting an output signal generated by a reaction between the biological substance and the specimen.

10. The particle according to claim 1, wherein each of the plurality of mesopores has a pore wall comprising a material selected from the group consisting of titanium oxide, tin oxide, and silicon oxide.

11. The particle according to claim 1, wherein each of the plurality of mesopores has a pore wall comprising silica.

12. The particle according to claim 1, wherein each of the plurality of mesopores has a pore wall made of a first material, and wherein a second material different from the first material is formed on a surface of each of the plurality of mesopores.

13. The particle according to claim 12, wherein an organic substance layer or an inorganic oxide layer is formed on the surface of each of the plurality of mesopores.

14. The particle according to claim 1, wherein each of the plurality of mesopores has a pore wall which is connected to the biological substance with an anchor.

15. The particle according to claim 1, wherein the biological substance is immobilized on each of the plurality of mesopores by electrostatic bonding.

16. The particle according to claim 1, wherein the biological substance is immobilized on each of the plurality of mesopores by noncovalent bonding.

* * * * *